US011058830B2

(12) United States Patent
Sienko et al.

(10) Patent No.: US 11,058,830 B2
(45) Date of Patent: Jul. 13, 2021

(54) ASSISTIVE DEVICE FOR SUBCUTANEOUS INJECTIONS OR IMPLANTS

(71) Applicant: THE REGENTS OF THE UNIVERSITY OF MICHIGAN, Ann Arbor, MI (US)

(72) Inventors: Kathleen Sienko, Ann Arbor, MI (US); Ibrahim Mohedas, Ann Arbor, MI (US); Amir Sabet Sarvestani, Hartsdale, NY (US); Corey Bertch, Canton, MI (US); Anthony Franklin, Swartz Creek, MI (US); Adam Joyce, Livonia, MI (US); Jacob McCormick, Goodrich, MI (US); Michael Shoemaker, Dearborn, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/093,672

(22) PCT Filed: Mar. 14, 2017

(86) PCT No.: PCT/US2017/022291
§ 371 (c)(1),
(2) Date: Oct. 15, 2018

(87) PCT Pub. No.: WO2017/180279
PCT Pub. Date: Oct. 19, 2017

(65) Prior Publication Data
US 2019/0184113 A1 Jun. 20, 2019

Related U.S. Application Data

(60) Provisional application No. 62/323,278, filed on Apr. 15, 2016.

(51) Int. Cl.
*A61M 5/42* (2006.01)
*A61M 5/142* (2006.01)
(Continued)

(52) U.S. Cl.
CPC ............ *A61M 5/425* (2013.01); *A61M 5/142* (2013.01); *A61M 5/42* (2013.01); *A61B 17/3403* (2013.01); *A61M 5/14* (2013.01); *A61M 37/0069* (2013.01)

(58) Field of Classification Search
CPC .. A61M 2025/0206; A61M 2025/0213; A61M 37/0069; A61M 5/425; A61M 5/42;
(Continued)

(56) References Cited

U.S. PATENT DOCUMENTS

| 1,934,046 A | * | 11/1933 | Demarchi | A61M 5/425 604/115 |
| 2,743,723 A | * | 5/1956 | Hein | A61M 5/425 604/115 |
| 4,451,253 A | * | 5/1984 | Harman | A61K 9/0024 604/60 |
| 4,664,651 A | * | 5/1987 | Weinshenker | A61B 17/135 600/490 |

(Continued)

FOREIGN PATENT DOCUMENTS

JP  2006521904 A  9/2006

OTHER PUBLICATIONS

International Application No. PCT/US2017/022291, International Search Report and Written Opinion, dated Jun. 19, 2017.

*Primary Examiner* — Nilay J Shah
(74) *Attorney, Agent, or Firm* — Marshall, Gerstein & Borun LLP

(57) ABSTRACT

An assistive device for subcutaneous injections or implants. The assistive device is placed under a blood pressure cuff that displaces the skin and subcutaneous tissues of a patient at an insertion site in order to allow guided insertion of a needle or implant applicator into a subcutaneous fat layer. The skin and subcutaneous tissue is displaced or drawn, via (Continued)

pressure applied by the blood pressure cuff, through an injection window of a device body into a hollow cavity of the device body. A guide channel leads from a front side of the device body into the hollow cavity, and an applicator of an adapter is inserted through the guide channel into the subcutaneous fat layer.

10 Claims, 7 Drawing Sheets

(51) Int. Cl.
    *A61M 37/00*     (2006.01)
    *A61M 5/14*     (2006.01)
    *A61B 17/34*     (2006.01)

(58) Field of Classification Search
CPC ........ A61M 5/3287; A61M 2005/1585; A61M 2005/1586; A61M 25/02; A61B 17/3403; A61B 2018/00464; A61B 5/6861; A61B 8/4227; A61B 5/0205
See application file for complete search history.

(56) References Cited

U.S. PATENT DOCUMENTS

| | | | |
|---|---|---|---|
| 4,753,636 A * | 6/1988 | Free | A61B 17/32093 604/115 |
| 5,108,378 A | 4/1992 | Firth et al. | |
| 5,873,856 A * | 2/1999 | Hjertman | A61M 5/46 604/117 |
| 2002/0077599 A1 | 6/2002 | Wojcik | |
| 2002/0107503 A1* | 8/2002 | Gordon | A61M 31/005 604/507 |
| 2003/0150044 A1* | 8/2003 | Hoy | A41D 13/08 2/125 |
| 2004/0044290 A1* | 3/2004 | Ward | A61B 5/022 600/490 |
| 2004/0242528 A1* | 12/2004 | Hagstrom | A61K 48/0075 514/44 A |
| 2007/0032819 A1* | 2/2007 | McEwen | A61B 17/1322 606/202 |
| 2008/0221510 A1 | 9/2008 | Van Der Graaf et al. | |
| 2009/0093761 A1 | 4/2009 | Sliwa et al. | |
| 2010/0137799 A1* | 6/2010 | Imai | A61M 5/158 604/115 |
| 2010/0137831 A1 | 6/2010 | Tsals | |
| 2015/0157787 A1* | 6/2015 | Cully | A61M 5/158 604/6.05 |

* cited by examiner ns or implants, and more specifically, to an assistive device placed under a blood pressure cuff that displaces the skin of a patient at an insertion site in order to allow guided insertion of a needle or implant applicator.

ASSISTIVE DEVICE FOR SUBCUTANEOUS INJECTIONS OR IMPLANTS

CROSS-REFERENCE TO RELATED APPLICATIONS

This application is the U.S. national phase of International Application No. PCT/US17/22291, filed Mar. 14, 2017, which claims the benefit of the filing date of U.S. Provisional Application No. 62/319,932, filed Mar. 15, 2016, which is hereby incorporated by reference in its entirety.

FIELD OF THE DISCLOSURE

This disclosure relates generally to an assistive device for subcutaneous injections or implants, and more specifically, to an assistive device placed under a blood pressure cuff that displaces the skin of a patient at an insertion site in order to allow guided insertion of a needle or implant applicator.

BACKGROUND

In many places throughout the world, access to health clinics, trained clinicians, and medical devices is limited due to inadequate infrastructure, a shortage of trained medical providers, and insufficient distribution networks. For example, Ethiopia has only 2.5 physicians per 100,000 people, a ratio which worsens in rural areas. In such areas, patients rely on care from community health workers. Twenty-three countries in sub-Saharan Africa employ community healthcare workers to provide services to 206 million women living in rural areas. Community healthcare workers provide largely educational services to rural populations in addition to low-level healthcare services such as blood pressure measurement, vaccine delivery, and overseeing medication delivery. Unfortunately, community healthcare workers do not have the expertise required to perform certain medical procedures. As a result, the adoption of certain medical procedures is far more limited than would be the case if trained physicians were more easily accessible. In particular, subdermal implants, such as implantable contraceptives, and subcutaneous injections are performed less frequently than would be the case if patients were able to obtain better medical care.

In sub-Saharan Africa, nearly half of married women of reproductive age have expressed the desire to space or limit their pregnancies, but only 1 in 7 are using modern contraception and only 1 in 40 uses long-term contraception. Worldwide, 113 million women have unmet contraceptive needs. Meeting these needs would prevent on the order of 54 million unintended pregnancies, avoid on the order of 26 million abortions, avert on the order of 7 million miscarriages, and prevent on the order of 79 thousand maternal and 1.1 million infant deaths every year. Intrauterine and subcutaneous implant contraceptive methods are the most effective reversible contraception methods available. Subcutaneous implants are single or double rods that contain etonogestrel and are inserted subdermally on the inner side of a woman's non-dominant arm. Single-rod devices (e.g., IMPLANON®, NEXPLANON®) can prevent pregnancy for up to three years while two-rod devices (e.g., JADELLE®, SINO-IMPLANT®) can prevent pregnancy for up to five years. In addition, implants do not require maintenance or effort on the part of the user, allow women to return to fertility quickly, and have very low failure rates. While the benefits of implantable contraceptives are significant, major barriers exist that prevent wider usage; namely, the training and skill required for performing insertion/removal procedures.

Currently, subcutaneous contraceptive implants are inserted free-hand by trained healthcare providers. This requires healthcare providers to precisely thread a large bore needle just beneath the skin along the underside of a women's arm to deploy the implant. If performed correctly, the contraceptive implant is left within the subcutaneous fat layer just beneath the skin. However, this freehand method can lead to implants being inserted too deeply in the fat layer or embedded in the muscle. Methods requiring high frequency ultrasound, trained technicians, skilled doctors, and even MRIs are needed to remove these deeply embedded implants, increasing the cost and time for removal, discomfort of the patient, and risk of complications. In some cases, healthcare providers need to cut away significant portions of muscle in order to remove the implant. Due to these issues, the World Health Organization recommends that only providers at the level of nurse/midwife or higher administer contraceptive implants in their current form. With the current free-hand insertion methodology, the governments of low- and middle-income countries would need to invest very heavily in training programs to expand access to contraceptive implants to rural areas and would still encounter improper insertions that require hospital-based removals that are not available to large proportions of the rural population.

SUMMARY OF THE DISCLOSURE

The current disclosure is directed to an assistive device that is secured by a blood pressure cuff and used to guide an implant or injection needle. The assistive device dramatically reduces the training required for administration of subdermal implants and subcutaneous injections. The assistive device reduces insertion errors across all levels of healthcare providers and ensures precise and reliable placement of an implant, which also allows for easy removal of an implant. The assistive device "task shifts" essential healthcare services from physicians to nurses, community healthcare providers, and other more readily available medical workers. As a result, the assistive device expands access to certain implant and injection procedures, which can improve healthcare in low and middle-income countries and make long-term contraception more widely accessible. Community healthcare workers do not have access to sterilizing equipment or chemicals in rural areas so the assistive device is made from disposable materials.

The assistive device has a device body that includes a clip or other attachment mechanism by which it can be attached to a blood pressure cuff. A skin-contacting surface of the device body has an injection window into a hollow cavity of the device body. A guide channel extends longitudinally along the device, parallel to the skin-contacting surface, from a front side of the device body into the hollow cavity. When the blood pressure cuff is inflated to a predetermined pressure, such as 40 mm HG, skin and subcutaneous tissue is raised through the injection window and into the hollow cavity. A needle may travel through the guide channel to deliver anesthesia or other medical fluids, either before insertion of an implant or as an independent procedure.

Generally, an adapter facilitates placement of an implant. Different implants have different adapter designs, but generally each adapter includes an applicator. When used in conjunction with the assistive device, the applicator of an adapter slides through the guide channel and into the raised subcutaneous tissue. Because the skin/tissue displacement through the injection window is controlled by the pressure of the blood pressure cuff, the applicator is inserted at an accurate depth parallel to the skin.

DETAILED DESCRIPTION

Figure 1A:
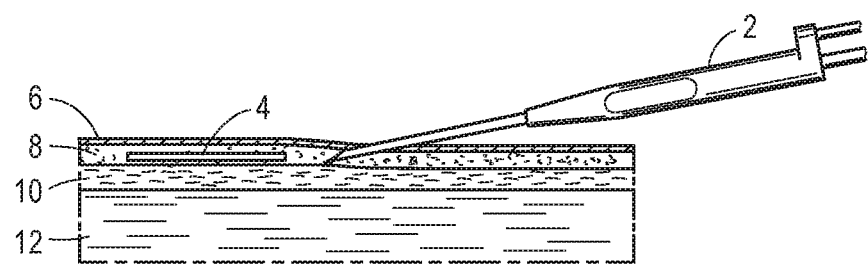
FIG. 1A illustrates a cross-sectional view of correct placement of an implant in a patient using a free-hand placement method.
Figure 1B:
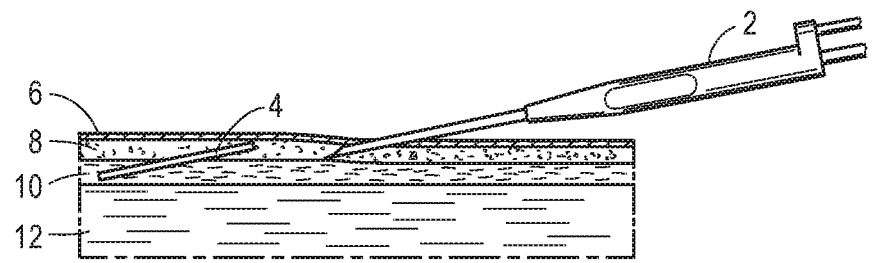
FIG. 1B illustrates a cross-sectional view of incorrect placement of an implant in a patient using a free-hand placement method.

FIGS. 1A and 1B illustrate correct and incorrect placement, respectively, of an implant 4 in the tissue of a patient using free-hand placement by a free-hand placement device 2. In FIG. 1A, the implant 4 is properly placed below the skin 6 in the subcutaneous fat layer 8 above the deeper fat layer 10 and muscle 12. In FIG. 1B, the implant is improperly placed at angle through the subcutaneous fat layer 8, deeper fat layer 10, and muscle 12. A placement such as that depicted in FIG. 1B can lead to painful complications requiring a trained physician for removal of the improperly placed implant and treatment of any resulting injury or infection.

Figure 2:
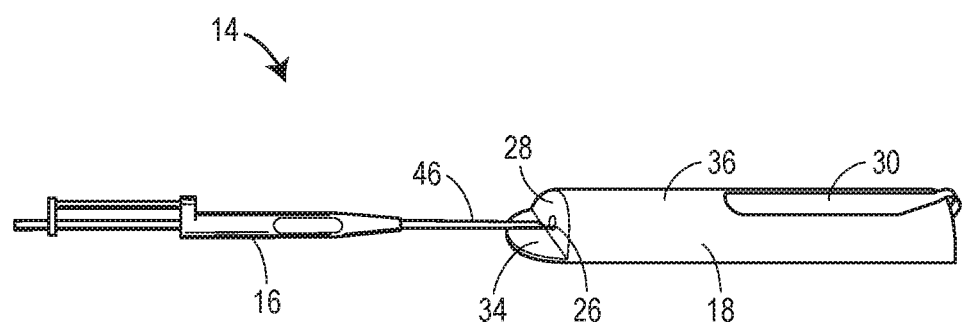
FIG. 2 illustrates a top isometric view of the assistive device of the present disclosure prior to the applicator of the adapter being inserted into the guide channel of the device body.

FIG. 2 illustrates a top isometric view of the assistive device 14 of the present disclosure designed to prevent improper placement of implants, such as that depicted in FIG. 1B. The assistive device 14 could be used to place subdermal implants, including contraceptive implants (such as IMPLANON®, NEXPLANON®, JADELLE®, SINOPLANT®, or NORPLANT®), pharmaceutical implants for infection prevent (such as SEPTOPAL®) or cancer treatment (such as ZOLADEX®), osmotic pumps, biodegradable implants, recreational implants, or embedded devices. The assistive device could also be used for subcutaneous injection. Such injections might deliver, for example, insulin for diabetes, local anesthesia, allergy tests, tuberculin, growth hormone, and epinephrine.

Figure 3:
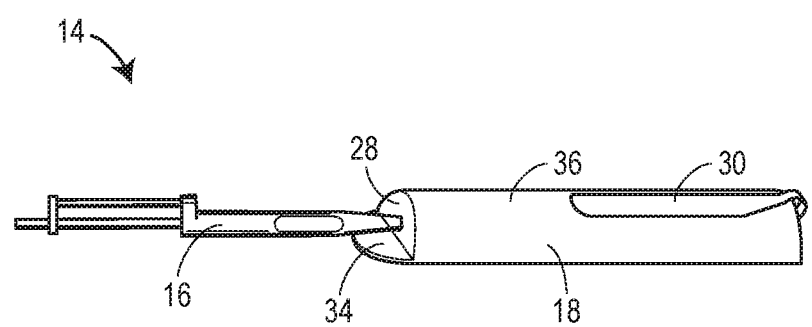
FIG. 3 illustrates a top isometric view of the assistive device of the present disclosure as the applicator of the adapter is inserted into the guide channel of the device body.
Figure 4:
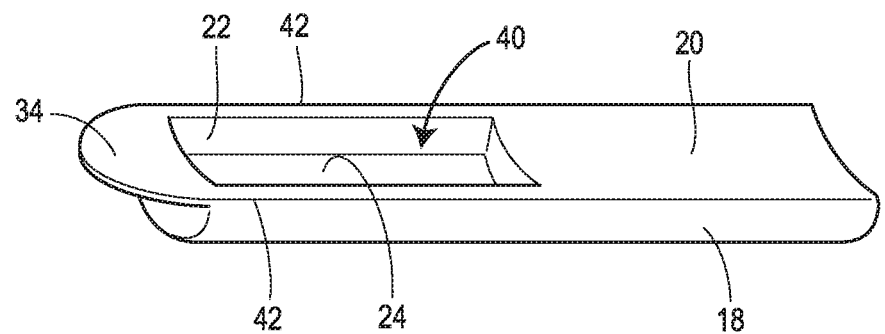
FIG. 4 illustrates a bottom isometric view of the device body of the assistive device of the present disclosure.

The assistive device 14 includes a device body 18 compatible with an adapter 16. The device body 18 has a clip or attachment mechanism 30 to secure it to a blood pressure cuff, and an indentation 36 to make it easier to put the clip 30 on the blood pressure cuff. In some embodiments, the device body further has a shield 34. As shown in FIG. 3, an applicator 46 of the adapter 16 is insertable at a front side 28 of the device body 18 into a guide channel 26 in the device body 18. FIG. 4 shows the device body 18 with the skin-contacting surface 20 visible. An injection window 22 in the skin-contacting surface 20 opens to an internal hollow cavity 24. The internal hollow cavity 24 has a top surface 40 to prevent skin and subcutaneous tissue from rising too much after a blood pressure cuff is pressurized.

In some embodiments within the scope of the present disclosure, edges 42 of the injection window 22 on the skin-contacting surface 20 are rounded to facilitate entry of the skin and subcutaneous tissue into the internal hollow cavity 24. In some embodiments within the scope of the present disclosure, the length of the device body 18 is just longer than a standard blood pressure cuff having a length of 9 cm in order for the front side 28 of the device body 18 to extend just beyond the end of the blood pressure cuff. In some embodiments within the scope of the present disclosure, the height of the device body 18 is optimized to ensure enough space for the hollow cavity 24 while minimizing overall height.

Figure 5:
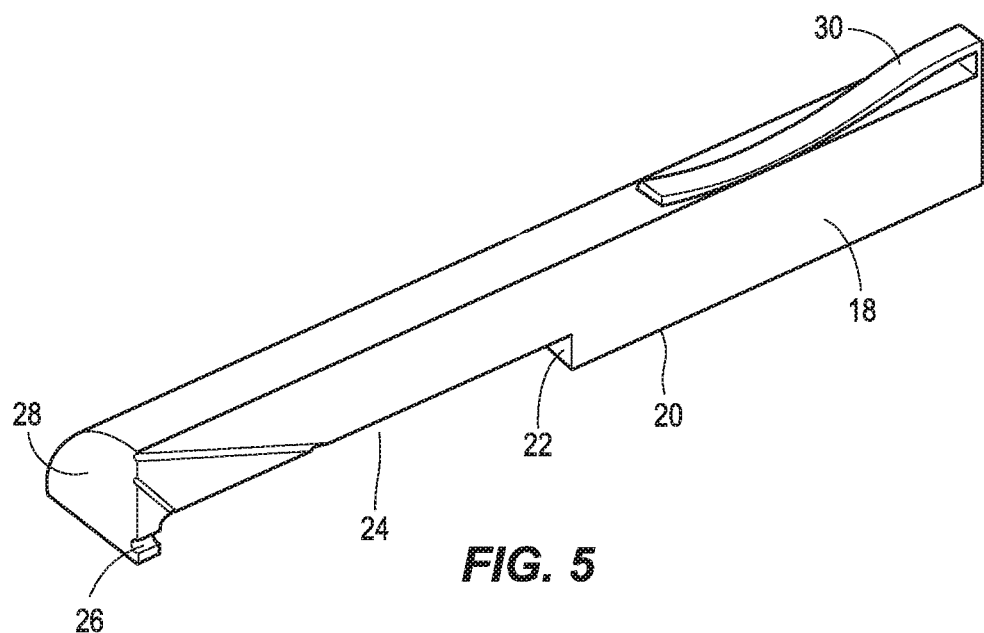
FIG. 5 illustrates a cross-sectional isometric view of the device body of the assistive device of the present disclosure.
Figure 6:
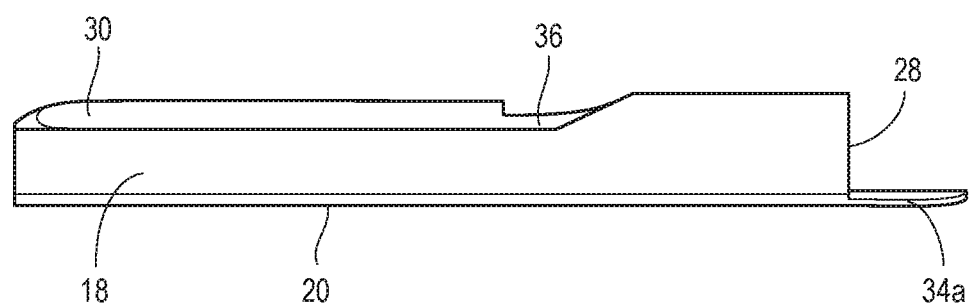
FIG. 6 illustrates a side view of the device body of the assistive device of the present disclosure.
Figure 7:
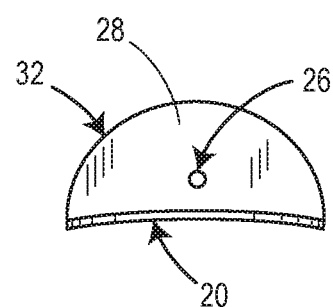
FIG. 7 illustrates a front view of the device body of the assistive device of the present disclosure.
Figure 8:
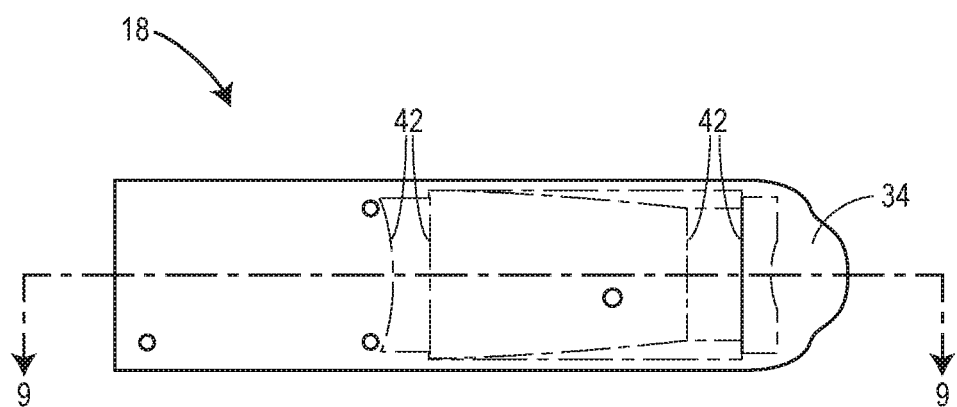
FIG. 8 illustrates a top view of the device body of the assistive device of the present disclosure.
Figure 9:
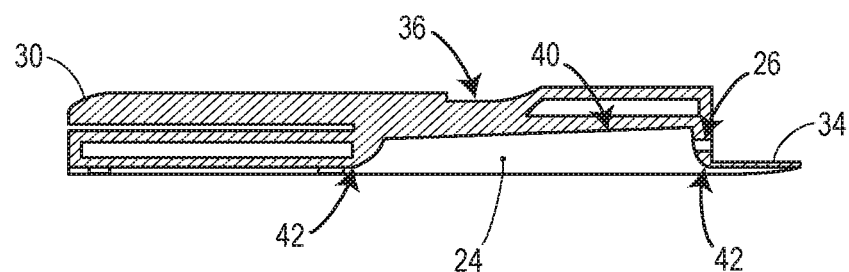
FIG. 9 illustrates a cross-sectional view of the device body of the assistive device of the present disclosure taken along line A-A of FIG. 8.

As can be seen in FIG. 5, a guide channel 26 extends from the front side 28 of the device body 18 into the hollow cavity 24. The diameter of the guide channel 26 is greater than a diameter of the applicator 46. In general, the diameter of the guide channel 28 is at least 0.5 mm. Although only one guide channel 26 is depicted in FIG. 5, in some embodiments within the scope of the present disclosure, a plurality of guide channels 26 may be provided so that the assistive device 14 is compatible with a variety of adapters 16. The shield 34 is provided to prevent skin from obscuring entry into the guide channel 26. The distance between the guide channel 26 and the top surface 40 of the hollow cavity 28 is greater than 1.5 mm but less than 10 mm. FIGS. 6-9 provide additional views of embodiments of the device body 18 within the scope of the present disclosure.

Figure 10A:
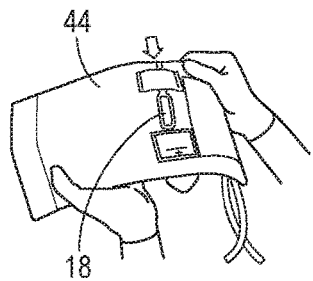
FIG. 10A illustrates the device body of the assistive device of the present disclosure being attached to a blood pressure cuff.
Figure 10B:
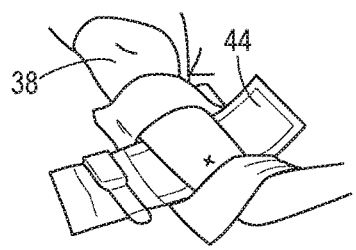
FIG. 10B illustrates the blood pressure cuff with the attached assistive device being secured around the arm of a patient.
Figure 10C:
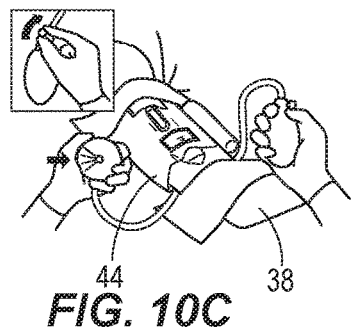
FIG. 10C illustrates the blood pressure cuff with the attached assistive device that is secured around the arm of the patient being inflated to a target pressure.
Figure 10D:
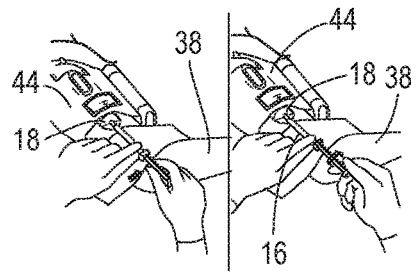
FIG. 10D illustrates a needle being inserted into the arm of the patient through the assistive device to deliver anesthesia on the left and the applicator of the adapter being inserted into the arm of the patient on the right in order to insert an implant.
Figure 10E:
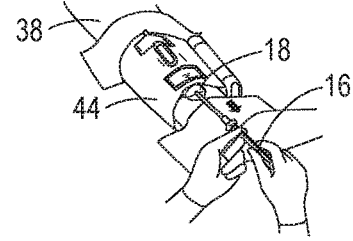
FIG. 10E illustrates the applicator of the adapter being removed from the device body of the assistive device.
Figure 10F:
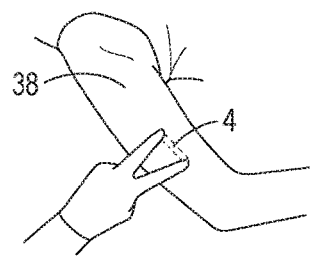
FIG. 10F illustrates the implant properly placed within the arm of a patient.

FIGS. 10A-10F depict placement of an implant 4 using an assistive device 14 of the present disclosure. Prior to the steps shown in FIGS. 10A-10F, the insertion site should be identified at 8-10 cm above the epicondyle on the underside of the arm, and the insertion site should be disinfected. As shown in FIG. 10A, the assistive device 14 is then clipped on to a blood pressure cuff 44. Then, as depicted in FIG. 10B, the blood pressure cuff 44 is secured around the arm 38 of a patient at the insertion site. As shown in FIG. 10C, the blood pressure cuff 44 is then inflated to a target pressure. An exemplary target pressure would be 40 mm Hg. On the left, FIG. 10D depicts insertion of a needle into the assistive device 14 and administration of anesthesia. On the right, FIG. 10D depicts insertion of the adapter 16 for purposes of placing an implant 4. FIG. 10E depicts removal of the adapter 16 after the implant 4 has been placed. FIG. 10F depicts accurate placement of the implant 4 in the arm 38 of the patient.

Figure 11A:
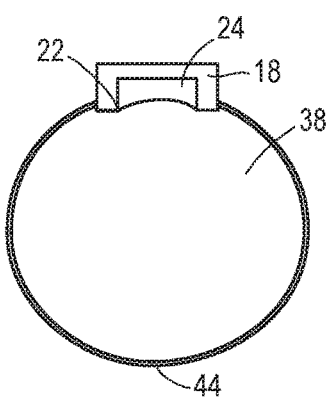
FIG. 11A illustrates a cross-sectional view of the assistive device secured on a patient's arm by a blood pressure cuff (not pictured).
Figure 11B:
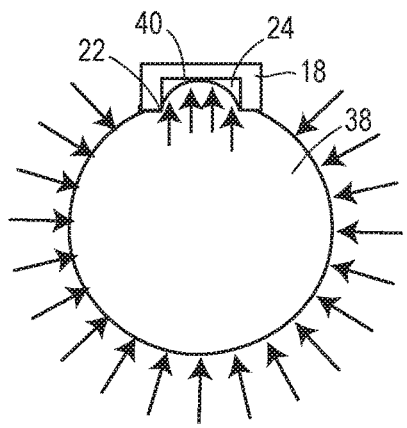
FIG. 11B illustrates a cross-sectional view of the skin and tissue of the patient's arm being pressed by the blood pressure cuff (not pictured) into the hollow cavity of the assistive device.

FIG. 11A depicts the device body 18 placed on the arm 38 of the patient. The skin 6 of the arm 38 is in contact with either the blood pressure cuff 44 or the device body 18 except at the injection window 22 and hollow cavity 24 of the device body 18. When the pressure of the blood pressure cuff 44 is increased, as shown in FIG. 11B, the skin 6 and subcutaneous tissues of the arm 38 are forced through the injection window 22 into the hollow cavity 24. The top surface 40 of the hollow cavity 24 prevents too much skin and subcutaneous tissue from entering the hollow cavity 24. The arm 38 in FIG. 11B is now ready for an injection or implant.

Figure 12A:
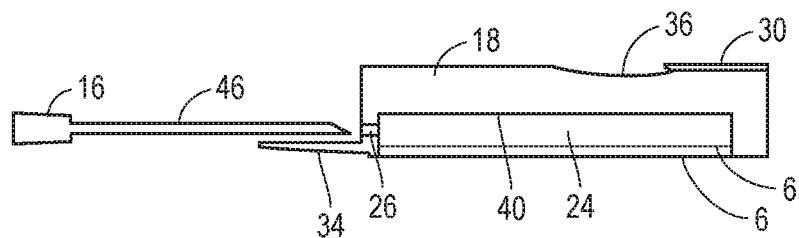
FIG. 12A illustrates a cross-sectional view of an assistive device along the longitudinal axis of the device when the assistive device is placed on the patient's skin prior to pressure being applied by a blood pressure cuff.
Figure 12B:
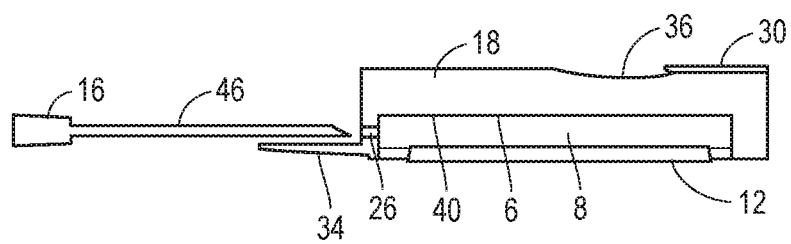
FIG. 12B illustrates the cross-sectional view of FIG. 11A as pressure is applied by the blood pressure cuff and underlying skin and subcutaneous tissue is drawn into a hollow cavity of the assistive device of the present disclosure.
Figure 12C:
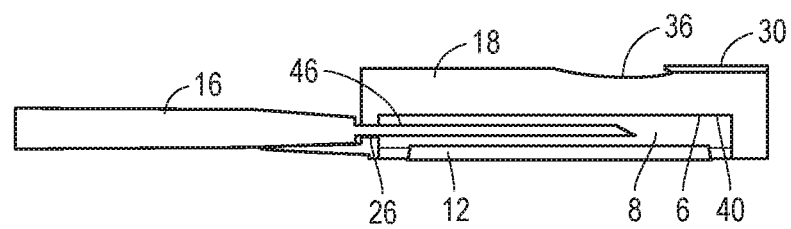
FIG. 12C illustrates the cross-sectional view of FIGS. 11A and 11B as pressure is applied by the blood pressure cuff and the applicator is inserted through the assistive device, through the skin, and into the patient.

FIG. 12A depicts the device body 18 and adapter 16 prior to pressure being applied. Skin 6 and the subcutaneous fat layer 8 are below the device body 18. The hollow cavity 24 is empty. FIG. 12B depicts the device body 18 and adapter 16 as pressure is applied. Skin 6 and the subcutaneous fat layer 8, as well as some muscle 12, are pulled into the hollow cavity 24. The top surface 40 is in contact with the skin 6. The applicator 46 of the adapter 16 is aligned with the subcutaneous fat layer 8 by the guide channel 26. FIG. 12C shows the applicator 46 of the adapter 16 being inserted through the guide channel 26 into the subcutaneous fat layer 8. The applicator 46 of the adapter 16 does not contact the muscle 12. The accurate placement of an implant 4 allows for easy removal when the implant 4 needs to be replaced.

While various embodiments are described herein, it will be understood that variations can be made thereto that are still within the scope of the appended claims.

What is claimed is:

1. A method of using an assistive device comprising:
attaching an assistive device to a pressure cuff, the assistive device including a device body, the device body having a skin-contacting surface having an injection window opening to a hollow cavity of the device body, the hollow cavity of the device body being at least partially defined by a top surface, a guide channel connecting a front side of the device body to the hollow cavity, the guide channel disposed in a direction parallel to the top surface of the hollow cavity, and an outer surface connected to an attachment mechanism;
securing the pressure cuff around an arm of a patient;
inflating the pressure cuff to a target pressure;
inserting an applicator of an adapter through the guide channel into the hollow cavity in the device body of the assistive device, the applicator having an implant therein; and
placing the implant in the patient via the applicator.

2. The method of using the assistive device of claim 1, wherein the target pressure is 40 mm Hg.

3. The method of using the assistive device of claim 1, and prior to the step of securing the pressure cuff around the arm of the patient, identifying an insertion site.

4. The method of using the assistive device of claim 3, wherein the insertion site is between eight and ten centimeters above an epicondyle on an underside of the arm of the patient.

5. The method of using the assistive device of claim 3, and prior to the step of securing the pressure cuff around the arm of the patient, disinfecting the insertion site.

6. The method of using the assistive device of claim 3, and in the step of inserting the applicator through the guide channel into the hollow cavity in the device body of the assistive device, inserting the applicator in a direction parallel to a skin contacting surface at the identified insertion site.

7. The method of using the assistive device of claim 1, and in the step of inflating the pressure cuff to the target pressure, forcing skin and subcutaneous tissues through the injection window of the device body into the hollow cavity of the device body.

8. The method of using the assistive device of claim 7, wherein the forcing the skin and subcutaneous tissues through the injection window of the device body into the hollow cavity of the device body includes sliding the skin along a curved edge of the injection window.

9. The method of using the assistive device of claim 1, wherein the step of placing the implant includes inserting the implant into a subcutaneous fat layer.

10. The method of using the assistive device of claim 1, wherein the implant is one of a contraceptive implant, a pharmaceutical implant, an osmotic pump, a biodegradable implant, a recreational implant, and an embedded device.

\* \* \* \* \*